United States Patent [19]

Hauser et al.

[11] Patent Number: 4,946,443
[45] Date of Patent: Aug. 7, 1990

[54] CATHETER INTRODUCER

[75] Inventors: Jean-Luc Hauser, Antibes; Bernard Tomatis, Magagnosc; Christian Sainte-Rose, Paris, all of France

[73] Assignee: Cordis Corporation, Miami, Fla.

[21] Appl. No.: 262,614

[22] Filed: Oct. 26, 1988

[30] Foreign Application Priority Data

Oct. 27, 1987 [FR] France .................. 87 14852

[51] Int. Cl.⁵ ............................................. A61M 5/18
[52] U.S. Cl. ............................ 604/165; 604/264; 604/900
[58] Field of Search ...................... 604/164–170, 604/264, 900; 128/760, 768

[56] References Cited

U.S. PATENT DOCUMENTS

| 2,623,520 | 12/1952 | Bamford, Jr. et al. | 604/165 |
| 3,352,306 | 11/1967 | Hirsch | 604/168 |
| 3,809,081 | 5/1974 | Loveless | 604/170 |
| 4,193,400 | 3/1980 | Loveless et al. | 604/168 |
| 4,317,445 | 3/1982 | Robinson | 604/168 |
| 4,636,200 | 1/1987 | Vaillancourt | 604/170 |
| 4,735,614 | 4/1988 | Yapp et al. | 604/165 |

FOREIGN PATENT DOCUMENTS

| 0716726 | 12/1931 | France | 604/169 |
| 2522507 | 9/1983 | France | 604/170 |

Primary Examiner—C. Fred Rosenbaum
Assistant Examiner—Denise W. DeFranco
Attorney, Agent, or Firm—Lockwood, Alex, FitzGibbon & Cummings

[57] ABSTRACT

A catheter introducer including a cannula, a stylet disposed within the cannula, and means for holding a catheter in close proximity to the cannula and stylet so that the tip of the catheter is positioned near the tip of the cannula after insertion within the human body. In the preferred embodiment, the stylet may be releasably locked in position within the cannula. The disclosed design allows the user to sample fluid through the tip of the inserted cannula and to inject medication into the insertion site without having to re-introduce a needle therein.

27 Claims, 1 Drawing Sheet

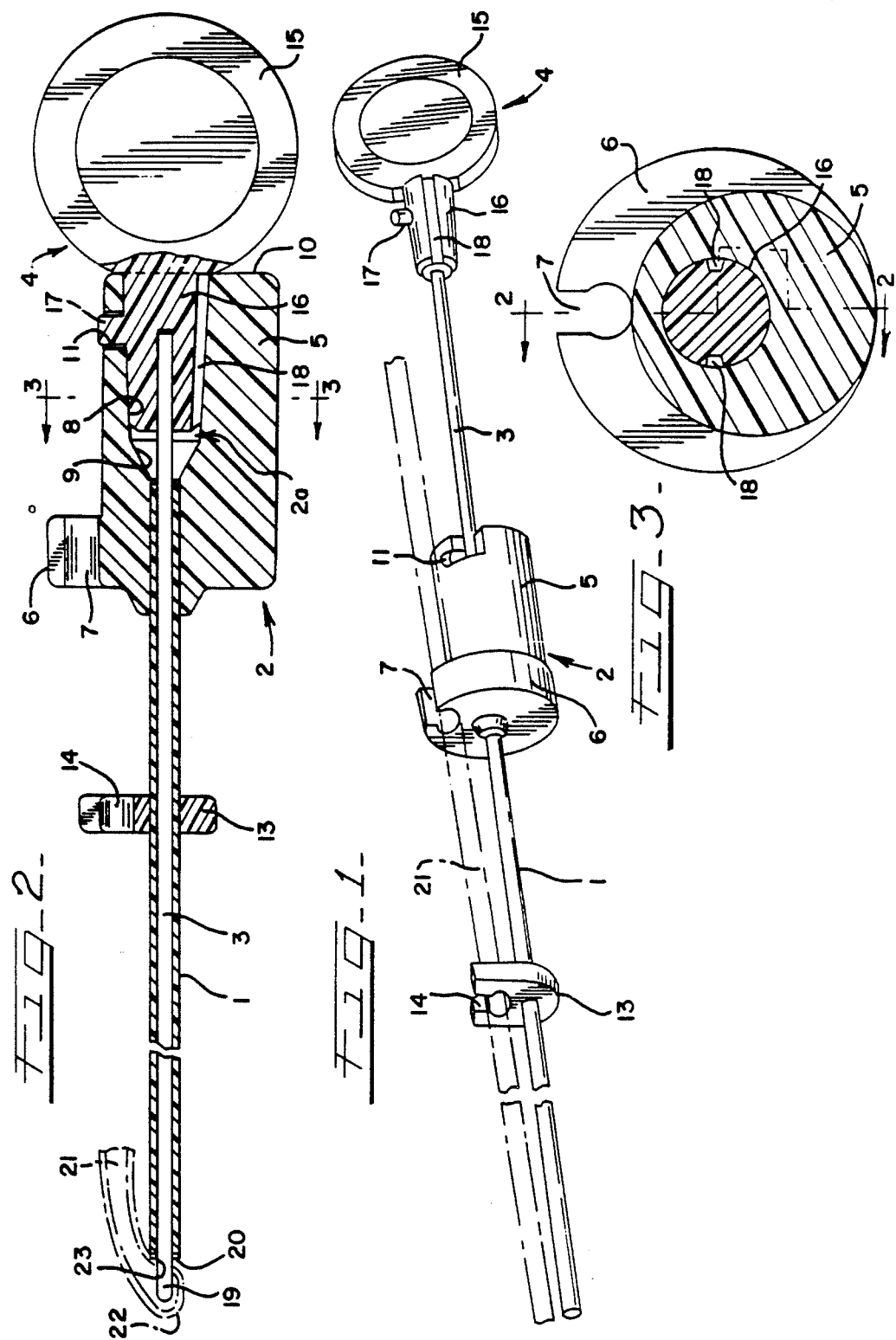

CATHETER INTRODUCER

BACKGROUND AND BRIEF DESCRIPTION OF THE INVENTION

This invention relates to a device for introducing a catheter into the human body. More specifically, this invention relates to a Ventricular Catheter Introducer (VCI) which includes a cannula, a stylet disposed within the cannula, and means for holding a catheter in close proximity to the cannula and stylet so that the tip of the catheter will be positioned near the tip of the cannula after insertion thereof. In the disclosed embodiment, the stylet may be releasably locked in position within the cannula. The disclosed design allows the user to sample fluid from the insertion site and to inject materials into the insertion site without the need to re-introduce a needle therein.

VCI devices are generally known in the art for introducing catheters into certain areas within the human body such as into a ventricle of the brain, for example. Catheters are generally manufactured with a flexible material having an opened end and a closed end. The closed end of the catheter is generally intended to be inserted into the body and is provided with a plurality of holes within the sidewalls thereof to allow fluid to pass. The opened end of the catheter is most often connected to an apparatus such as a valve or a pump. The interior of such a catheter is generally inaccessible, thereby preventing the use of a simple stylet for providing some rigidity to the catheter structure when the catheter is inserted into the desired area of the body.

Various VCI devices are known in the art which provide a cannula having a stylet releasably disposed therein in such a manner that the free end of the stylet protrudes from the free end of the cannula. The protruding stylet forms a shoulder with the free end of the cannula. The protruding end of the stylet can be inserted into one of the pores or holes in the side walls of the catheter so that the catheter will abut against the aforementioned shoulder thereby connecting the closed end of the catheter with the free end of the introducer. The catheter may then be placed within the body at the desired site by inserting the introducer/catheter combination therein. After insertion, the closed end of the catheter is freed from the stylet by retracting the stylet into the cannula. If desired, the stylet and the cannula can then be removed from the insertion site while leaving the catheter in position.

Prior art introducers generally are limited in several aspects. For example, in order to perform an injection near the inserted end region of the catheter, it has been necessary to reintroduce a needle into the insertion area. Re-introduction of a needle is generally undesirable because of the potential danger, especially when carried out in the brain. Further, it is difficult to determine whether the injection has been made in the required position, i.e. near the inserted end of the catheter. Prior art introducers generally include no means for retaining the inserted stylet in its proper position within the cannula during insertion of the introducer and the catheter. Consequently, the stylet may retract into the cannula and be unintentionally disconnected from the catheter, requiring that the operation be restarted. Additionally, prior art introducers contain no means by which the user can sample the fluid at the insertion site in order to determine whether the catheter has been positioned at the desired drainage area. In the insertion of a ventricular catheter, for example, the detection of cerebrospinal fluid would indicate that the catheter has been inserted into the desired position, i.e. within the ventricle of the brain.

The present invention overcomes the above-discussed limitations of the prior art introducers by providing a catheter introducer including a tubular cannula, a stylet removably retained within the cannula, and means for holding a catheter in close proximity to the cannula and stylet. The VCI of the present invention allows a user to introduce and properly position a catheter within the body. Means are provided to releasably lock the stylet within the cannula and to thereby prevent the unintentional retraction of the stylet into the cannula during insertion of the introducer and catheter into the human body. Additionally, the cannula is provided with a body portion which is dimensioned to engage the end of a syringe. In this manner, injections may be made without the need to re-introduce a needle into the insertion site. In this arrangement of parts, the user can be certain that the injection is placed at or near the end of the inserted catheter. Discharge means are also provided which allow body fluids to pass through the introducer as an indication that the desired insertion area has been reached.

Accordingly, it is an object of the present invention to provide a catheter introducer including a cannula, a stylet disposed within the cannula and means for holding a catheter in close proximity t the cannula and stylet;

It is another object of the present invention to provide the catheter introducer wherein the stylet may be releasably locked within the cannula to prevent the unintentional retraction of the stylet into the cannula during insertion of the catheter into the human body;

It is still another object of the present invention to provide a catheter introducer which can engage a syringe to thereby allow the placement of an injection near the tip of the inserted catheter;

It is still another object of the present invention to provide a catheter introducer having means for allowing body fluids to pass therethrough to indicate that a desired insertion area has been reached.

BRIEF DESCRIPTION OF THE DRAWINGS

These and other objects and advantages of the present invention will be appreciated by those skilled in the art upon consideration of the remainder of the disclosure including the detailed description of the invention and the drawings, wherein:

FIG. 1 is a perspective view of a catheter introducer according to the present invention;

FIG. 2 is a side elevational view, partially in section, of a catheter introducer in accordance with the present invention and taken along 2—2 line of FIG. 3;

FIG. 3 is a transverse sectional view of the catheter introducer of FIG. 2 taken along the 3—3 line thereof.

DETAILED DESCRIPTION OF THE INVENTION

Referring to FIGS. 1-3, a catheter introducer according to the present invention is shown. The catheter introducer includes a tubular cannula 1 having a body member 2 mounted on an end thereof. The body member 2 of the cannula 1 includes a cylindrical portion 5 and a flange portion 6. The flange portion 6 is provided with a catheter retention slot 7 therein. The cylindrical portion 5 further includes a conical recess 2a dimensioned in the shape of dual truncated cones 8 and 9 and extending into the cylindrical portion 5 from an end 10 of the body member 2. As further explained below, the conical recess 2a is dimensioned to accommodate the end of a syringe therein. As shown in FIG. 2, truncated cone 8 extends from the end 10 of the body member 2 into the cylindrical portion 5. Truncated cone 9 extends from the innermost end of the truncated cone 8 to the end of the cannula 1 which is mounted in the body member 2 and opens into the vertex of the conical recess 2a. A laterally extending slot 11 is provided in the cylindrical portion 5 of the body member 2. The slot 11 extends down from the surface and through the wall of the cylindrical portion 5 and into the truncated cone 8 of conical recess 2a.

A stylet 3 is provided and is slideably received within tubular cannula 1, as shown in FIGS. 1 and 2. The stylet 3 is provided with an extractor member 4 mounted on one end thereof. The extractor 4 includes a gripping portion 15 which extends from and is affixed to a neck portion 16. The neck portion 16 is dimensioned to fit within the truncated cone 8 of conical recess 2a within the body member 2. A stud 17 protrudes from neck portion 16 and is dimensioned to be received within the laterally extending slot 11 to thereby lock the extractor 4 in an operative engagement with the body member 2. At least one longitudinal slot or groove 18 is provided along the length of the neck portion 16 whereby body fluids may pass from the cannula 1, into the truncated cone 9 and through the truncated cone 8 along the slot 18 when the catheter introducer is inserted within the human body. This aspect of the invention is further explained below. An additional catheter clip 13 is slideably disposed along the length of the cannula 1 and is provided with a cannula retention slot 14 which in preferably aligned with the cannula retention slot 7 in the flange 6 of body member 2.

In use, the body member 2 is operatively engaged with the extractor 4 by insertion of the neck portion 16 into the truncated cone 8 of conical recess 2a. In this manner, the stylet 3 is disposed within the cannula and is releasably locked therein by proper positioning of the stud 17 within the locking slot 11 of cylindrical portion 5. In this arrangement of parts, the stylet tip 19 will protrude slightly from the cannula 1, essentially as shown in FIG. 2. The stylet tip 19 is simultaneously secured in its protruding position by the above-mentioned locking relationship of the stud 17 and slot 11.

When releasably locked within the cannula 1, the stylet tip 19 and the tip of cannula 1 form a shoulder at the end of cannula 1, generally indicated at 20. In its locked position, stylet tip 19 will hold the catheter 21 by insertion of the tip 19 into a pore or hole 23 in the sidewall of the catheter end 22. The shoulder 20 provides a stop for the controlled insertion of the stylet tip 19 into the pore or hole 23 of the catheter 21. During insertion into the body, the catheter is held within the retention slots 7 and 14 and in close proximity to the introducer. The locking relationship between stud 17 and slot 11 prevent the stylet 3 from being inadvertently retracted within the cannula 1 during insertion.

When the catheter 21 is positioned at a desired drainage area within the body, the design of the present invention will allow fluid flow between the inner wall of the cannula 1 and the stylet 3, and into the conical hole 9 of the body member 2. The body fluid will then pass through the truncated cone 8 via the fluid leakage means which are provided in the form of at least one longitudinal slot 18 in the surface of neck portion 16. In this manner, the user can then detect the presence of these body fluids as they exit the slots 18 at the end 10 of the body member 5. The presence of such fluids will indicate that the catheter 21 is positioned at the desired drainage area within the body.

Following insertion, the stylet 3 may be withdrawn from the cannula 1 by first rotating the extractor 4 to thereby facilitate the withdrawal of stud 17 from slot 11. The stylet 19 may then be retracted into the cannula 1 by removing neck portion 16 from the conical recess 2a thereby releasing the catheter end 22 from the tip 19. Once the stylet 3 has been completely removed from within cannula 1, the end of a syringe can be positioned within the truncated cone 8 in the body member 2 to inject a substance such as antibiotics, for example, through the cannula 1 and into the drainage area near the tip 22 of the inserted cannula 21. In this manner, the need to re-introduce a needle to perform the above discussed injection is avoided thereby eliminating the potential dangers involved therewith and also insuring that the injected substance is placed within the body at or near the inserted tip 22 of the cannula 21.

While the embodiments of the present invention have been discussed and described above, it will be understood that various changes and modifications may be made by those skilled in the art without departing from the true spirit and scope of the invention, as defined in the following claims.

What is claimed is:

1. A catheter introducer for positioning a catheter within the human body, the catheter introducer comprising:
    a tubular cannula having a body member mounted at one end thereof, said body member having a recess formed therein, said recess extending from an end of said body member to said cannula, such that said end of said cannula opens into said recess;
    a stylet reversibly positioned in a sliding engagement within said cannula, said stylet having an extraction member mounted at one end thereof and a stylet tip at the other end thereof, said extraction member including a neck portion dimensioned to fit within said recess of said body member, said stylet being affixed to and extending from said neck portion; and
    catheter retention mans including a clip for releasably retaining a catheter in close proximity adjacent to said cannula during insertion into an area of the body.

2. The catheter introducer of claim 1, further comprising locking means for releasably locking said extraction member within said recess of said body member.

3. The catheter introducer of claim 2, wherein said locking means include a stud affixed to said neck portion of said extraction member, and a slot provided in said body member, said slot being dimensioned to receive said stud therein when said neck portion is positioned within said recess.

4. The catheter introducer of claim 1, wherein said neck portion includes fluid leakage means, said leakage means being in fluid communication with said cannula when said neck portion is positioned within said recess, said leakage means allowing fluid to flow from said cannula and through said recess of said body member.

5. The catheter introducer of claim 4, wherein said leakage means include at least one longitudinal slot provided on the surface of said neck portion.

6. The catheter introducer of claim 1, wherein said recess is a conical recess and said cannula opens into the vertex thereof.

7. The catheter introducer of claim 1 wherein said catheter retention means includes a flange associated with said body member, said flange having a retention slot therein, said clip being positioned along the length of said cannula, said clip and said retention slot dimensioned to receive a catheter therein.

8. The catheter introducer of claim 7 wherein said catheter retention means further includes said stylet tip, said tip dimensioned for insertion within a pore of said catheter, said tip forming a shoulder with said cannula to provide a stop for said catheter once said tip is inserted within said pore, whereby said catheter is retained on said tip and within said clip and said retention slot during insertion into an area of the body.

9. A catheter introducer for positioning a catheter within the human body, the catheter introducer comprising:
 a tubular cannula having a body member mounted at one end thereof, said body member having a conical recess formed therein, said recess extending from an end of said body member to said cannula, such that said end of said cannula opens into said conical recess;
 a stylet reversibly positioned in a sliding engagement within said cannula, said stylet having an extraction member mounted at one end thereof and a stylet tip at the other end thereof, said extraction member including a neck portion dimensioned to fit within said conical recess of said body member, said stylet being affixed to and extending from said neck portion;
 locking means for releasably locking said extraction member within said conical recess of said body member, said locking means including a stud affixed to said neck portion of said extraction member, and a slot provided in said body member, said slot being dimensioned to receive said stud therein when said neck portion is positioned within said conical recess; and
 catheter retention means including a clip for releasably retaining a catheter in close proximity adjacent to said cannula during insertion into an area of the body.

10. The catheter introducer of claim 9, wherein said neck portion includes fluid leakage means, said leakage means being in fluid communication with said cannula when said neck portion is positioned within said conical recess, said leakage means allowing fluid to flow from said cannula and through said conical recess of said body member.

11. The catheter introducer of claim 10, wherein said leakage means include at least one longitudinal slot provided on the surface of said neck portion.

12. The catheter introducer of claim 9 wherein said catheter retention means includes a flange associated with said body member, said flange having a retention slot therein, said clip being positioned along the length of said cannulas, said clip and said retention slot dimensioned to receive a catheter therein.

13. The catheter introducer of claim 12 wherein said catheter retention means further includes said stylet tip, said tip dimensioned for insertion within a pore of said catheter, said tip forming a shoulder with said cannula to provide a stop for said catheter when said top is inserted within said pore, whereby said catheter is retained on said tip and within said clip and said retention slot during insertion into an area of the body.

14. A catheter introducer for positioning a catheter within the human body, the catheter introducer comprising:
 a tubular cannula having a body member mounted at one end thereof, said body member having a recess formed therein, said recess extending from an end of said body member to said cannula, such that said end of said cannula opens into said recess;
 a stylet reversibly positioned in a sliding engagement within said cannula, said stylet having an extraction member mounted at one end thereof and a stylet tip at the other end thereof, said extraction member including a neck portion dimensioned to fit within said recess of said body member, said stylet being affixed to and extending from said neck portion; and
 catheter retention means for releasably retaining a catheter in close proximity adjacent to said cannula, said catheter retention means including a flange associated with said body member, said flange having a retention slot therein and a clip positioned along the length of said cannula, said clip and said retention slot dimensioned to receive a catheter therein.

15. The catheter introducer of claim 14 wherein said catheter retention means further includes said stylet tip, said tip dimensioned for insertion within a port of said catheter, said tip forming a shoulder with said cannula to provide a stop for said catheter once said tip is inserted within said pore, whereby said catheter is retained on said tip and within said clip and said retention slot during insertion into an area of the body.

16. The catheter introducer of claim 14, further comprising locking means for releasably locking said extraction member within said recess of said body member.

17. The catheter introducer of claim 16 wherein said locking means include a stud affixed to said neck portion of said extraction member, and a slot provided in said body member, said slot being dimensioned to receive said stud therein when said neck portion is positioned within said recess.

18. The catheter introducer of claim 14, wherein said neck portion includes fluid leakage means, said leakage means being in fluid communication with said cannula when said neck portion is positioned within said recess, said leakage means allowing fluid to flow from said cannula and through said recess of said body member.

19. The catheter introducer of claim 18, wherein said leakage means include at least one longitudinal slot provided on the surface of said neck portion.

20. The catheter introducer of claim 14, wherein said recess is a conical recess and said cannula opens into the vertex thereof.

21. A catheter introducer for positioning a catheter within the human body, the catheter introducer comprising:
 a tubular cannula having a body member mounted at one end thereof, said body member having a conical recess formed therein, said recess extending from an end of said body member to said cannula, such that said end of said cannula opens into said conical recess;

a stylet reversibly positioned in a sliding engagement within said cannula, said stylet having an extraction member mounted at one end thereof and a stylet tip at the other end thereof, said extraction member including a neck portion dimensioned to fit within said conical recess of said body member, said stylet being affixed to and extending from said neck portion;

locking means for releasably locking said extraction member within said conical recess of said body member, said locking means including a stud affixed to said neck portion of said extraction member, and a slot provided in said body member, said slot being dimensioned to receive said stud therein when said neck portion is positioned within said conical recess; and catheter retention means for releasably retaining a catheter in close proximity adjacent to said cannula, said catheter retention means including a flange associated with said body member, said flange having a retention slot therein and a clip positioned along the length of said cannula, said clip and said retention slot dimensioned to receive a catheter therein.

22. The catheter introducer of claim 21, wherein said catheter retention means further includes said stylet tip, said tip dimensioned for insertion within a pore of said catheter, said tip forming a shoulder with said cannula to provide a stop for said catheter when said tip is inserted within said pore, whereby said catheter is retained on said tip and within said clip and said retention slot during insertion into an area of the body.

23. The catheter introducer of claim 21, further comprising locking means for releasably locking said extraction member within said recess of said body member.

24. The catheter introduced of claim 23, wherein said locking means include a stud affixed to said neck portion of said extraction member, and a slot provided in said body member, said slot being dimensioned to receive said stud therein when said neck portion is positioned within said recess.

25. The catheter introducer of claim 21, wherein said neck portion includes fluid leakage means, said leakage means being in fluid communication with said cannula when said neck portion is positioned within said recess, said leakage means allowing fluid to flow from said cannula and through said recess of said body member.

26. The catheter introduce of claim 25, wherein said leakage means include at least one longitudinal slot provided on the surface of the said neck portion.

27. The caterer introducer of claim 21, wherein said recess is a conical recess and said cannula opens into the vertex thereof.

* * * * *

UNITED STATES PATENT AND TRADEMARK OFFICE
CERTIFICATE OF CORRECTION

PATENT NO. : 4,946,443

DATED : August 7, 1990

INVENTOR(S) : Jean-Luc Hauser et al.

It is certified that error appears in the above-identified patent and that said Letters Patent is hereby corrected as shown below:

Col. 2, line 30, "t" should read --to--.
Col. 3, line 36, "in" should read --is--.
Col. 4, line 49, "mans" should read --means--.
Col. 5, line 64, "cannulas" should read --cannula--.
Col. 6, line 2, "top" should read --tip--; line 33, "port" should read --pore--.
Col. 8, line 9, "introduced" should read --introducer--; line 21, "introduce" should read --introducer--; and line 24, "caterer" should read --catheter--.

Signed and Sealed this

Twenty-fifth Day of February, 1992

Attest:

HARRY F. MANBECK, JR.

*Attesting Officer*  *Commissioner of Patents and Trademarks*